(12) United States Patent
Levine (10) Patent No.: US 10,780,663 B2
(45) Date of Patent: Sep. 22, 2020

(54) ROSIN PRESSES AND RELATED METHODOLOGIES

(71) Applicant: Aaron Levine, Aguanga, CA (US)

(72) Inventor: Aaron Levine, Aguanga, CA (US)

( * ) Notice: Subject to any disclaimer, the term of this patent is extended or adjusted under 35 U.S.C. 154(b) by 325 days.

(21) Appl. No.: 15/818,556

(22) Filed: Nov. 20, 2017

(65) Prior Publication Data

US 2019/0152179 A1    May 23, 2019

(51) Int. Cl.
| | |
|---|---|
| *B30B 9/04* | (2006.01) |
| *B30B 9/06* | (2006.01) |
| *B30B 15/00* | (2006.01) |
| *B30B 15/06* | (2006.01) |
| *C09F 1/00* | (2006.01) |
| *A61K 36/185* | (2006.01) |
| *B30B 13/00* | (2006.01) |

(52) U.S. Cl.
CPC .............. *B30B 9/06* (2013.01); *A61K 36/185* (2013.01); *B30B 9/04* (2013.01); *B30B 13/00* (2013.01); *B30B 15/0052* (2013.01); *B30B 15/064* (2013.01); *C09F 1/00* (2013.01)

(58) Field of Classification Search
CPC ... B30B 15/064; B30B 13/00; B30B 15/0052; B30B 15/34; B30B 9/06; B30B 9/04; A61K 36/185; C09F 1/00; C09F 1/02
USPC .......................................... 100/37, 110, 315
See application file for complete search history.

(56) References Cited

U.S. PATENT DOCUMENTS

| | | | |
|---|---|---|---|
| 2015/0374025 A1* | 12/2015 | Evans ................... | B65D 77/04 99/495 |
| 2016/0296464 A1* | 10/2016 | Lindsay ............... | A61K 36/185 |
| 2018/0008655 A1* | 1/2018 | Weikel ................. | A61K 36/185 |
| 2018/0257326 A1* | 9/2018 | Sitnik .................. | B30B 15/064 |
| 2018/0297313 A1* | 10/2018 | Katz ........................ | B30B 9/04 |

* cited by examiner

*Primary Examiner* — Jimmy T Nguyen
(74) *Attorney, Agent, or Firm* — Buche & Associates, P.C.; John K. Buche; Bryce A. Johnson (57) ABSTRACT

The following pertains to a horizontally-situated high capacity rosin press capable of applying heat and pressure in a chamber to extract and collect rosin from inserted plant materials. The extracted rosin is capable of being collected via gravity-induced drainage, eliminating the need for manual separation of rosin and remaining plant materials.

1 Claim, 7 Drawing Sheets

FIG. 8C

ROSIN PRESSES AND RELATED METHODOLOGIES

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

The disclosed subject matter is in the field of rosin presses.

Background of the Invention

Plants often contain essential oils and resins (sap) that have various medicinal, recreational, and cosmetic uses. For instance, cannabis use has been legalized recently in several States and many residents in those areas often use cannabis resin recreationally or medicinally on a regular basis. So, it comes as no surprise that various processes have been developed for extracting resins and essential oils from plants.

Initially, harsh solvents (including light hydrocarbons like butane or propane) were used to chemically extract the resins and oils from plants. But, chemical extraction involves a complicated separation process to purify the extracted resins. Therefore, a need arose for non-chemical extraction techniques and processes for removing resins and oils from plants.

Recently, various rosin processes have been developed for extracting plant resin/oil. Instead of chemical solvents, rosin is a process that combines heat and pressure to extract resin or oil from plants. The process is mechanical and viewed as a more organic and natural process, as opposed to chemical extraction of resin or oils.

Known rosin presses involve applying downward pressure to gathered-plants on a hot plate so that resin is released. For instance, the Sasquash™ brand rosin press by Support The Roots of Murrieta, Calif., U.S.A. manufactures several versions of an upright rosin press wherein the face of a foot or hand operated hydraulic piston extends downward to press plants positioned on a hot plate. Once the resin is released, the plant pulp is separated from the resin so that the resin can be gathered up from the hot plate.

Although capable of producing resin, vertical (top down) rosin presses are not satisfactory for every situation. Separating the pulp and removing the resin from the hotplate can be tedious and time consuming. Also, such vertical rosin presses cannot process a large amount of resin at once because the downward pressure from the hydraulic piston can cause too much resin to spew radially over all sides of the hotplate. Thus, a need exists for improved resin presses and related methodologies without the drawbacks associated with known resin presses.

SUMMARY OF THE INVENTION

In view of the foregoing, an object of this specification is to disclose a high capacity rosin press. In a preferred embodiment, the resin press is defined by a reinforced cage that is positioned on a chassis, where the cage encloses a horizontally situated hydraulic piston for moving a heated ram face plate into a heated chamber that has been loaded with gathered plants. Suitably, the chamber may be top-loaded with gathered plants and features a drain for extracting by gravity any resin from the chamber after the plants have been pressed within the hot chamber by the hot ram face plate. Suitably, the cage may include a built-in rack underneath the chamber drain for collecting any resin pressed out of the gathered plants. In a preferred embodiment, the hydraulic piston is oil-based and operated by a foot or hand pump. Preferably, the cage includes an oil and pressure gauge for monitoring the operation of the pump and hydraulic piston.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which.

In the figures, the following reference numerals correspond to the associated components of the improved rosin press:

Improved rosin press—1000;
  Cage—1100;
    Cross frame panels—1110;
    Sheet metal cover—1130;
    Load hole—1131;
  Chassis—1200;
    Wheeled footer H-frame—1210;
    Upright H frames—1220;
    Support post—1211;
    Cross bar—1212;
    Second support post —1221;
    Second cross bar—1222;
  Pump—1300;
  Oil reservoir—1400;
  Hydraulic piston—1500;
  Ram face plate—1600;
  Chamber—1700;
  Chamber face plate—1800;
  Heating element—1900;
  Ram face—2000.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

Disclosed is a high capacity rosin press. In a preferred embodiment, the rosin press is defined by a reinforced cage that is positioned on a chassis, where the cage encloses a horizontally situated hydraulic piston for moving a heated ram face plate into a heated chamber that has been loaded with gathered plants. Suitably, the chamber may be top-loaded with gathered plants and features a drain for extracting by gravity any resin from the chamber after the plants have been pressed. The more specific aspects of the disclosed improvement to rosin presses are disclosed with reference to the appended figures.

Figure 1:
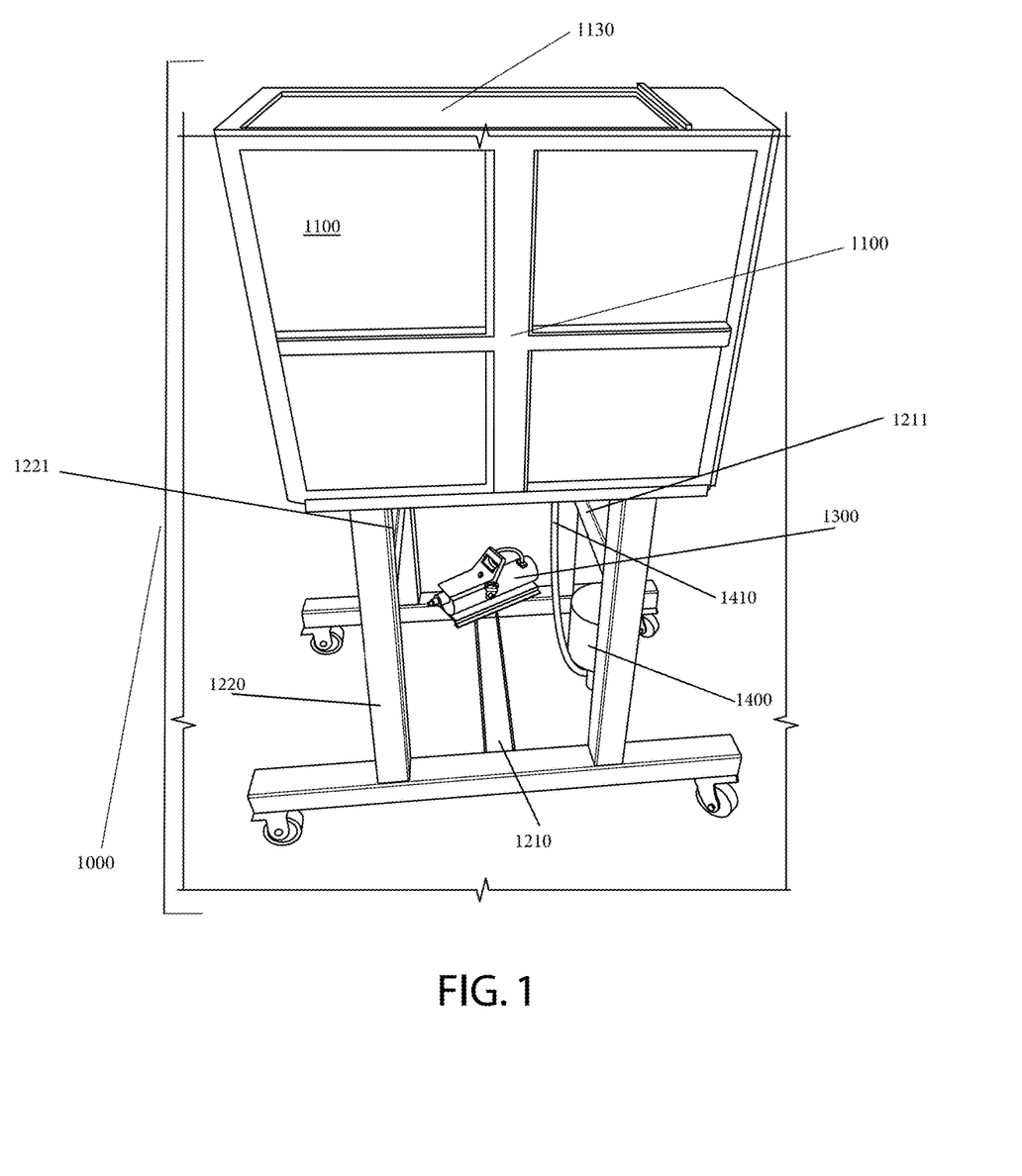
FIG. 1 is rear perspective view of an improved rosin press.
Figure 2:
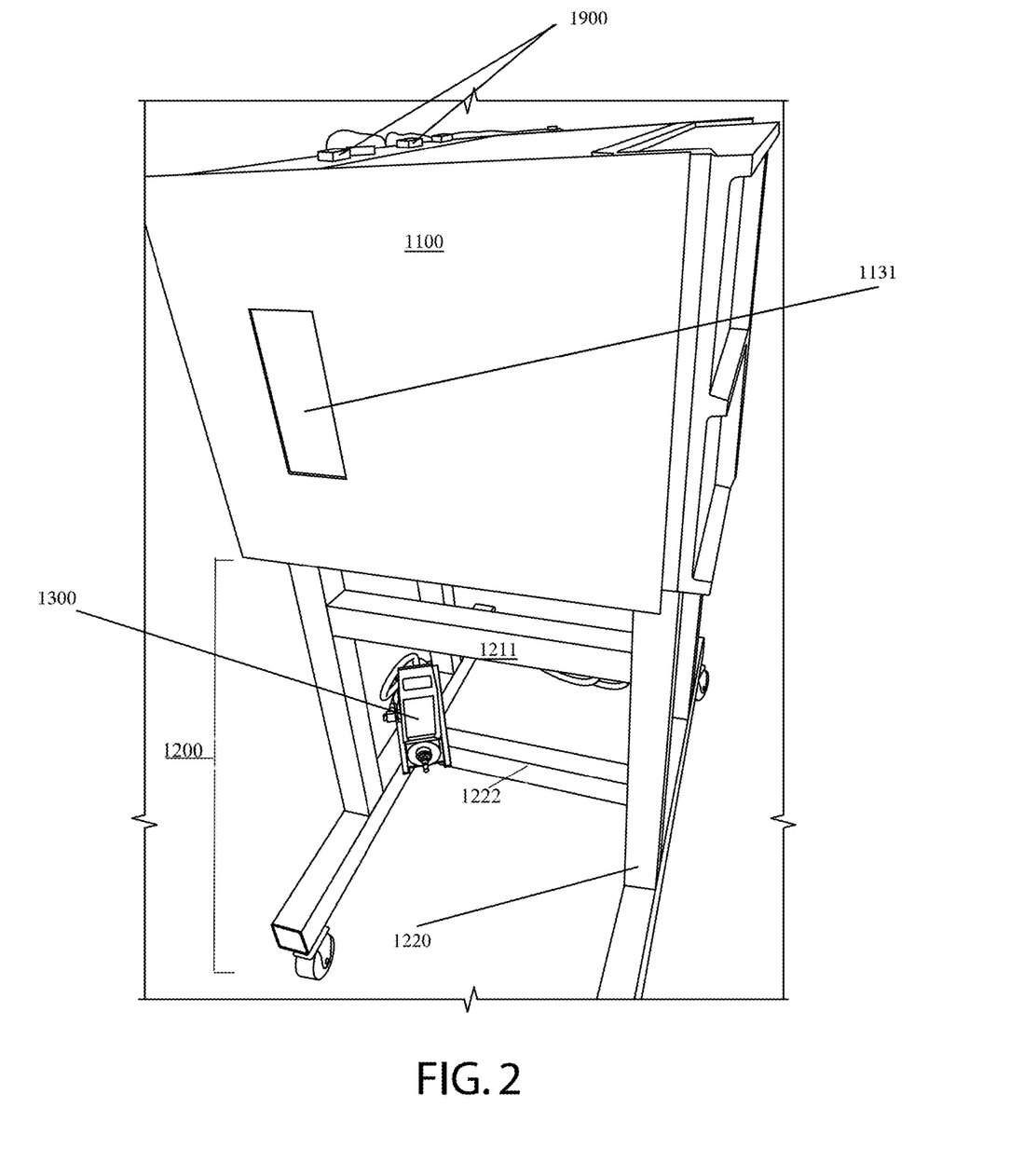
FIG. 2 is a left-side perspective view of the improved rosin press of FIG. 1.

FIG. 1 is a rear perspective view of an improved rosin press 1000. FIG. 2 is a left-side perspective view of the improved rosin press 1000. As shown in these figures, the improved rosin press 1000 is externally defined by a cage 1100 and a chassis 1200.

Figure 3:
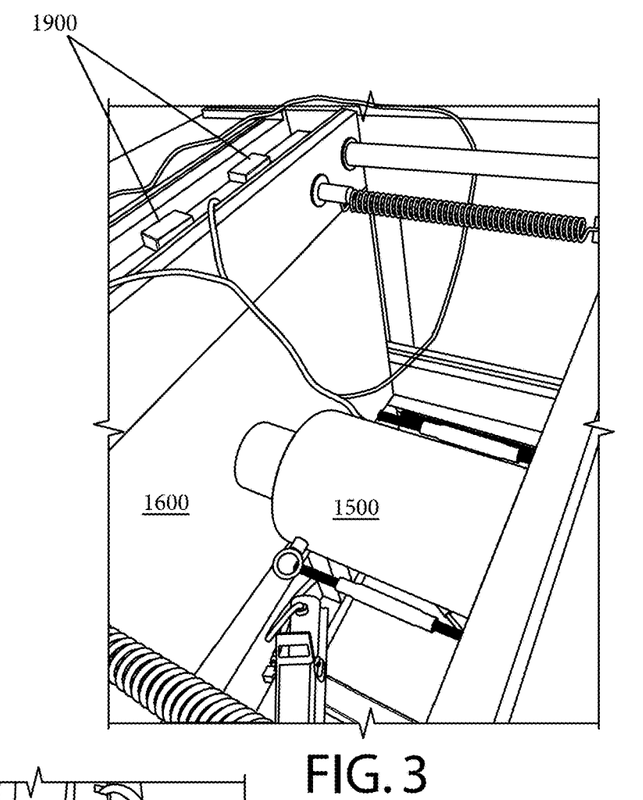
FIG. 3 is a top-down internal view of the improved rosin press of FIGS. 1 and 2.
Figure 4:
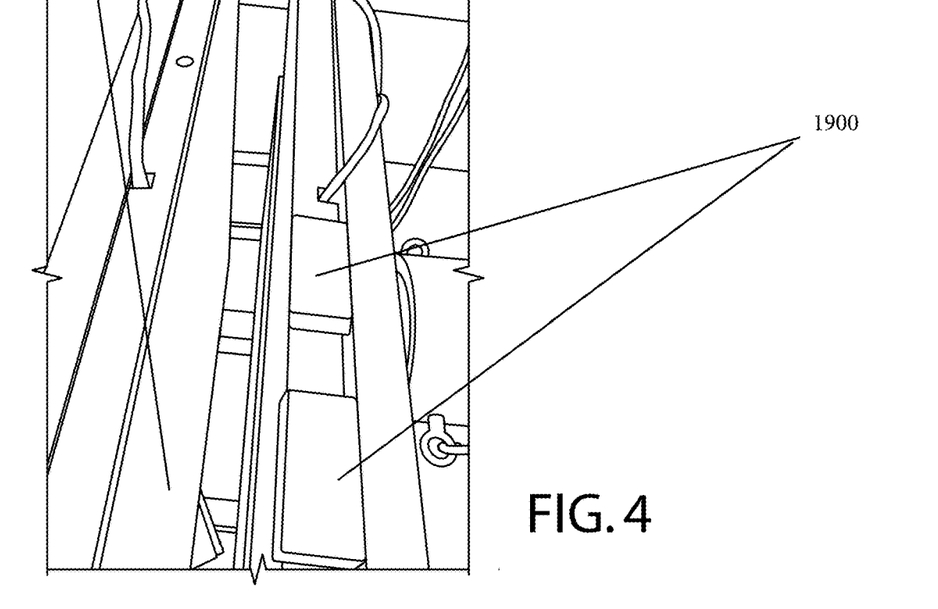
FIG. 4 is another top-down internal view of the improved rosin press of FIGS. 1 through 3.

FIGS. 1 and 2 illustrate the cage 1100. As shown, the cage 1100 is suitably defined by a six-sided hollow box. FIG. 3 is a top-down internal view of the improved rosin press of FIGS. 1 and 2. FIG. 4 is another top-down internal view of the improved rosin press of FIGS. 1 through 3. As shown in FIGS. 1 and 2, the front and back of the box are defined by reinforced cross-frame panels 1110. In a preferred embodiment, the cross frame panels 1110 are defined by a rectangular (30"×24"×1") steel panel that is reinforced by 30"× 1"×6" top and bottom steel bars, 22"×1"×6" side bars, a center upright bar defined by three 22"×¾"×6" steel plates, and a cross bar or bars defined by three 28"×1"×4" steel plates. Suitably, the steel may be A36 Steel. As discussed in greater detail with reference to FIG. 4, the front inner side of the front panel 1110 defines a chamber face plate 1800 that supports the chamber 1700. Referring now to FIG. 2, the side walls of the box are defined by a sheet metal cover 1130 with a load hole 1131 for accessing the chamber 1700.

FIGS. 1 and 2 illustrate the chassis 1200. As shown in the figure, the chassis 1200 may suitably be defined by a wheeled footer H-frame 1210 and two upright H-frames 1220. Suitably, each H-frame features two support posts 1211, 1221 and a cross bar 1212, 1222. As shown, the posts 1221 of the upright frame 1220 are mounted on opposite sides 1211 of and across the footer H-frame 1210. As shown, the cage 1100 is suitably mounted to the upright ends of the two upright H-frames 1300. The footer H frame may suitably feature wheels so 1230 so that the press 1000 may be mobile.

FIGS. 1 through 4 illustrate the hydraulic piston 1500. Referring to FIGS. 3 and 4, the cage 1100 may suitably house a hydraulic piston 1500 connected to a foot pump 1300 and oil reservoir 1400 for moving the ram face plate 1600 by hydraulic pump action into the chamber 1700. In a preferred embodiment, the foot pump 1300 is secured to the footer H-frame 1210 of the chassis 1200. Suitably, the foot pump moves oil through the piston in a hydraulic action via the oil reservoir 1400 and associated tubing 1410. As shown in FIG. 1 through 4, the piston is fixedly secured to the inside of the back panel 1110 in the center of the center upright bar on one side of the piston and the ram face plate 1700 on the other side of the piston. In a preferred embodiment, the hydraulic piston 1500 and pump 1300 is capable of exerting one hundred tons of force.

Figure 5A:
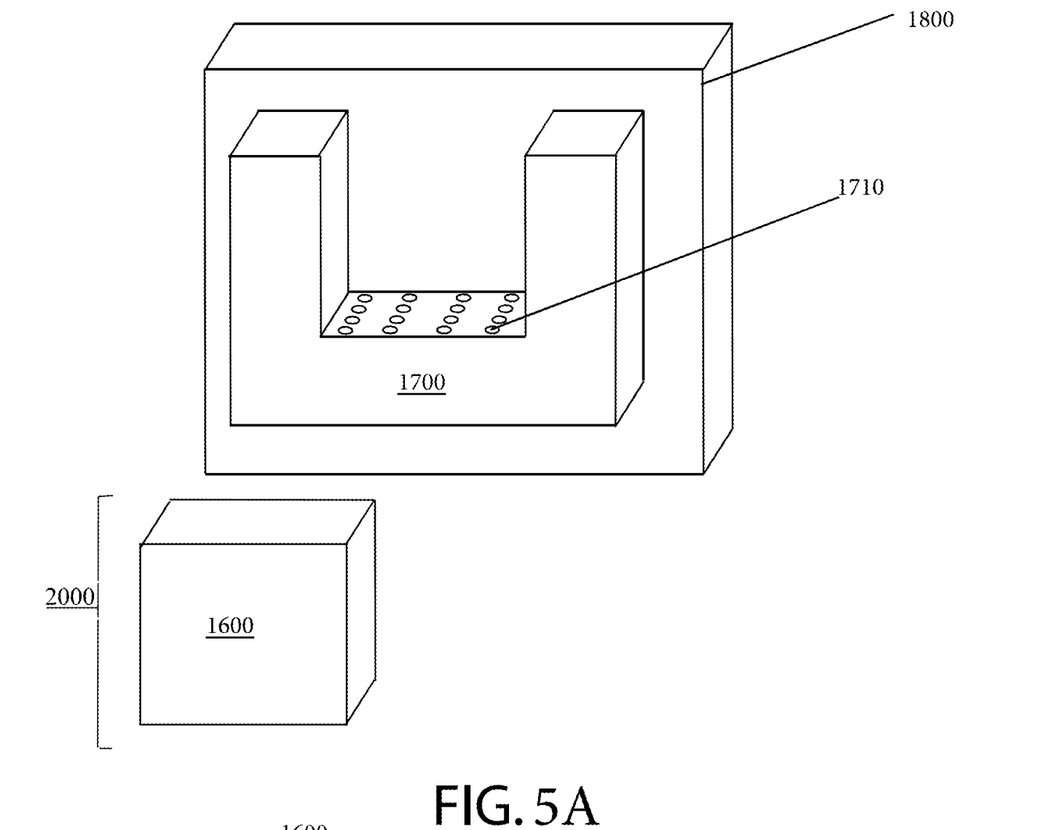
FIG. 5A is a perspective schematic of the chamber and ram face plate of the improved rosin press of FIGS. 1 through 4.
Figure 5B:
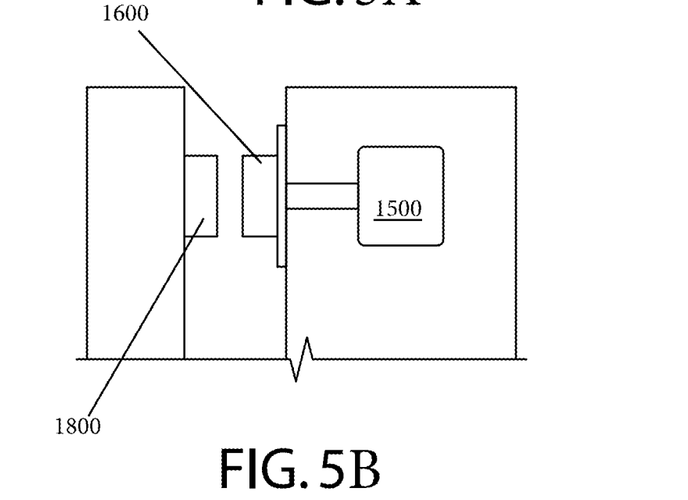
FIG. 5B side view schematic of the chamber and ram face plate of the improved rosin press.

As discussed above, hydraulic action between the pump 1300 and the piston 1500 operate to move the ram face plate 1600 inside of the chamber 1700. FIGS. 3 and 4 are top down internal views of the improved rosin press 1000. In a preferred embodiment, the heating elements 1900 are fixated to the upper surface of the ram face plate 1600 inside the chamber 1700. FIG. 5A is a perspective schematic of the chamber 1700 with drain holes 1710 housing the ram face plate 1600 of the improved rosin press 1000. FIG. 5B is a side view schematic of the chamber 1700 and the hydraulic piston 1500 that provides the force that pushes the ram face plate 1600 towards the chamber face plate 1800. In a preferred embodiment, the plant materials are loaded in between the ram face plate 1600 and the chamber face plate 1800. The force provided from the hydraulic piston 1500 propels the ram face plate 1600 laterally towards the chamber face plate 1800, pressing the plant materials in between the face plates.

Figure 6A:
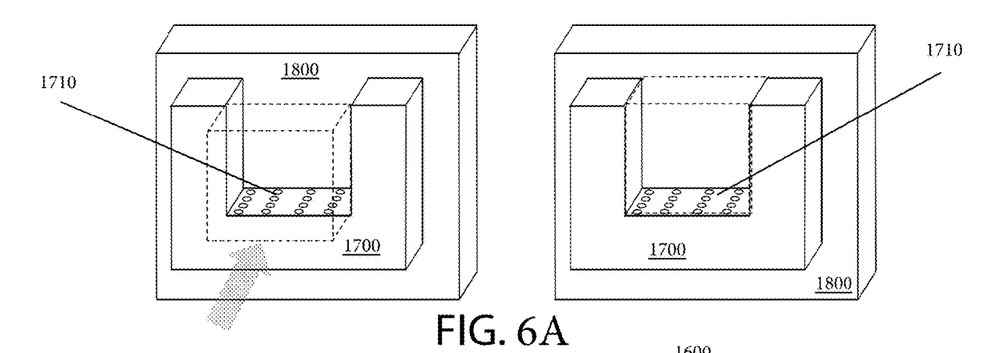
FIG. 6A is a closing operational perspective view of the chamber and ram face plate of the improved rosin press of FIGS. 1 through 4.

FIG. 6A is a closing operational perspective view of the chamber 1700 and ram face plate 1600 (shown in broken lines) of the improved rosin press 1000 within the cage 1100. The chamber 1700 exhibits drain holes 1710 to permit gravity-induced drainage of extracted rosin from the combination of heat and pressure when the ram face plate 1600 and chamber face plate 1800 press inserted plant materials. In one embodiment, the chamber 1700 may be loaded with plant materials from the side of the chamber 1700.

Figure 6B:
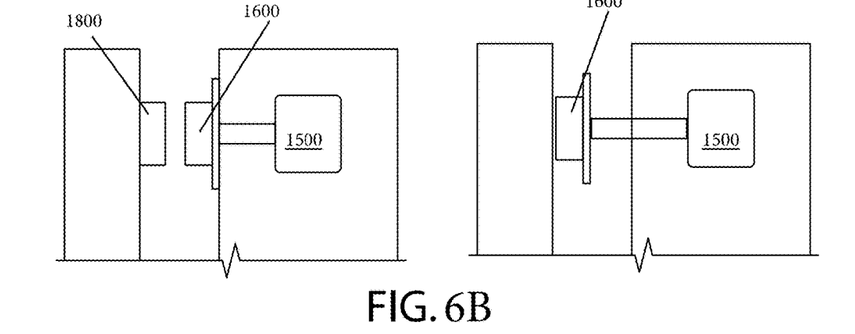
FIG. 6B is a side operational view of the chamber and ram face plate of the improved rosin press of FIGS. 1 through 4.

FIG. 6B is a side operational view of the chamber 1700 and ram face plate 1600 of the improved rosin press 1000. The hydraulic piston 1500 provides a force that propels the ram face plate 1600 laterally towards the chamber face plate 1800, exerting a pressing force on plant materials inserted between the two plates.

Figure 6C:
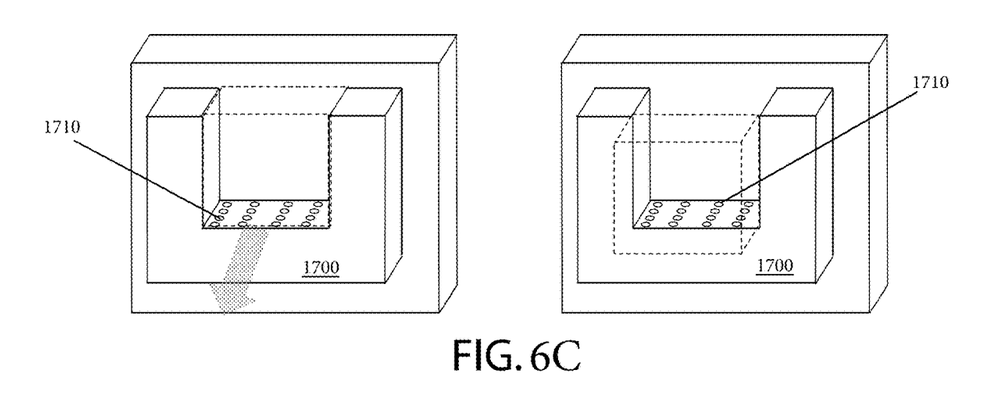
FIG. 6C is an opening operational view of the chamber and ram face plate of the improved rosin press of FIGS. 1 through 4.

FIG. 6C is an opening operational view of the chamber 1700 with drain holes 1710 and ram face plate 1600 of the improved rosin press 1000 showing the extraction of material from the chamber 1700.

Figure 7:
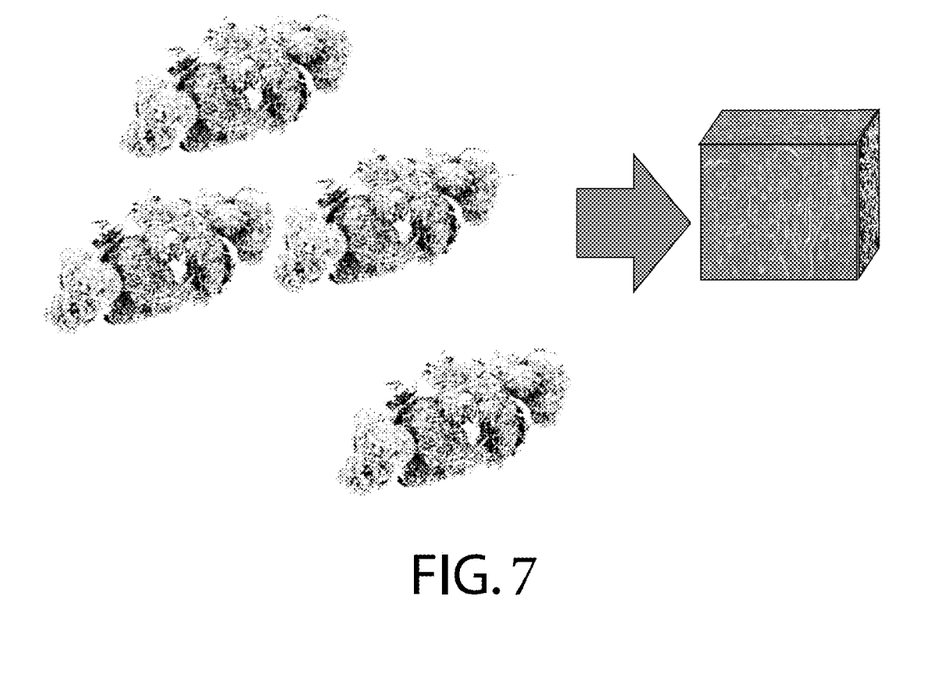
FIG. 7 is a schematic for gathering plants for placement in the improved rosin press.

FIG. 7 is a schematic for gathering plants for placement in the improved rosin press 1000. In one embodiment, the improved rosin press 1000 accommodates rosin bags containing pre-pressed concentrated rosin patties. Suitably, the improved rosin press 1000 accommodates rosin bags having the dimensions 22"×22", 8.5"×8.5", and 13"×13". In another embodiment, the improved rosin press 1000 exhibits propriety magnets to secure bags of rosin patties vertically within the improved rosin press 1000.

Figure 8A:
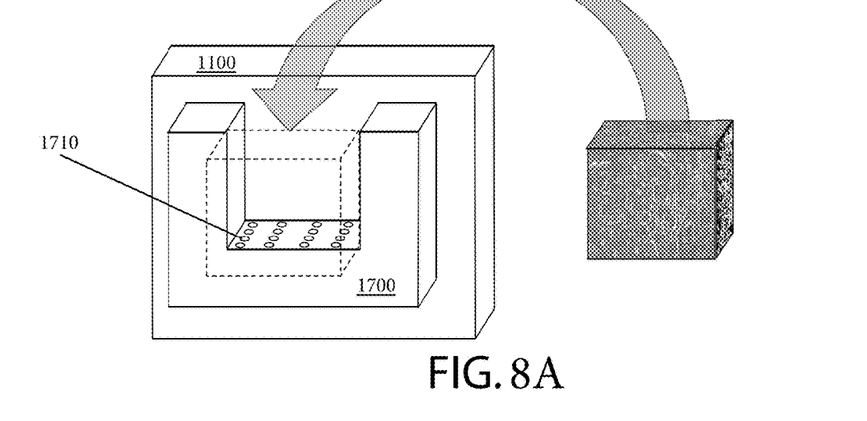
FIG. 8A is an load operation schematic of the chamber and ram face plate of the improved rosin press.
Figure 8B:
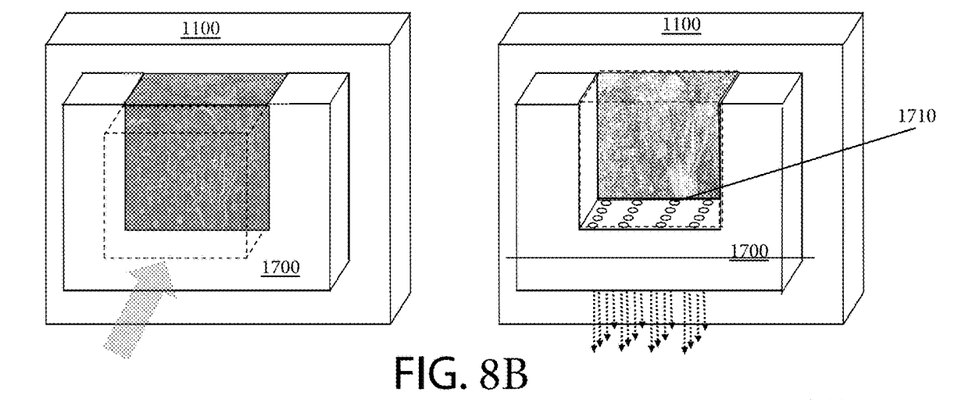
FIG. 8B is a press operation schematic of the chamber and ram face plate of the improved rosin press; and, FIG. 8C is an extraction schematic of the chamber of the improved rosin press.

FIG. 8A is a load operation schematic of the chamber 1700 with drain holes 1710 and ram face plate 1600 of the improved rosin press 1000 housed within the cage 1100. In a typical embodiment, the chamber 1700 may be top-loaded with plant materials. In another embodiment, the chamber 1700 may be loaded horizontally as shown in FIG. 8B. FIG. 8B is a press operation schematic of the chamber 1700 and ram face plate 1600 of the improved rosin press 1000 housed within the cage 1100 showing the extraction of plant material and gravity-induced drainage of rosin produced through the drain holes 1710.

Figure 8C:
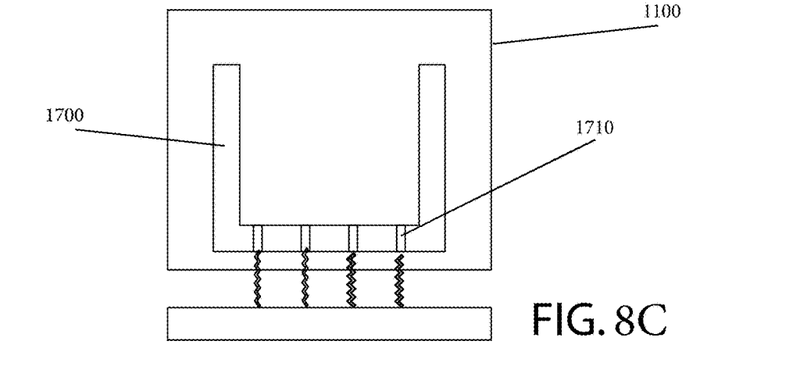

FIG. 8C is an extraction schematic of the chamber 1700 of the improved rosin press 1000 with the plant material removed and subsequent gravity-powered drainage of rosin extracted from the chamber 1700 through the drain holes 1710.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting to the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

I claim:

1. A method of controlling heat and pressure to extract rosin from plant materials comprising the steps of:
    obtaining a rosin press comprising a reinforced caged positioned within a chassis, a hydraulic piston that is situated horizontally within the chassis, a heated chamber housing a heated ram face plate, the heated ram face plate capable of movement inside the heated chamber;
    obtaining plant materials;
    inserting the plant materials into the heated chamber, adjusting a position of the plant materials until at a desire location within the heated chamber;
    controlling heat and pressure applied to the plant materials by the heated chamber and the heated ram face plate with a hand or foot pump;
    controlling the applied pressure and heat to press resin from the plant materials; and,
    collecting resin produced from pressing the plant materials by gravity-induced drainage through a drain in the heated chamber.

\* \* \* \* \*